US010286394B2

(12) United States Patent
Hori et al.

(10) Patent No.: US 10,286,394 B2
(45) Date of Patent: May 14, 2019

(54) ANALYSIS CHIP AND SAMPLE ANALYSIS APPARATUS

(71) Applicant: Takano Co.,Ltd., Nagano (JP)

(72) Inventors: Kazutaka Hori, Tokyo (JP); Tamotsu Minegishi, Tokyo (JP); Shinya Yamamoto, Tokyo (JP); Takamitsu Godo, Tokyo (JP)

(73) Assignee: Takano Co., Ltd., Nagano (JP)

( * ) Notice: Subject to any disclaimer, the term of this patent is extended or adjusted under 35 U.S.C. 154(b) by 78 days.

(21) Appl. No.: 15/311,132

(22) PCT Filed: May 12, 2015

(86) PCT No.: PCT/JP2015/063691
§ 371 (c)(1),
(2) Date: Nov. 14, 2016

(87) PCT Pub. No.: WO2015/174429
PCT Pub. Date: Nov. 19, 2015

(65) Prior Publication Data

US 2017/0080419 A1 Mar. 23, 2017

(30) Foreign Application Priority Data

May 15, 2014 (JP) ................................ 2014-101541

(51) Int. Cl.
*G01N 1/00* (2006.01)
*B01L 3/00* (2006.01)
(Continued)

(52) U.S. Cl.
CPC ....... *B01L 3/502715* (2013.01); *B01L 3/5023* (2013.01); *B01L 3/50273* (2013.01);
(Continued)

(58) Field of Classification Search
CPC ...................................................... G01N 1/00
See application file for complete search history.

(56) References Cited

U.S. PATENT DOCUMENTS 5,248,479 A 9/1993 Parsons et al.
5,639,428 A 6/1997 Cottingham
(Continued)

FOREIGN PATENT DOCUMENTS

EP 0417305 A1 3/1991
JP H05-302930 A 11/1993
(Continued)

OTHER PUBLICATIONS

International Search Report issued in PCT/JP2015/063691; dated Aug. 18, 2015.
(Continued)

*Primary Examiner* — Jyoti Nagpaul
(74) *Attorney, Agent, or Firm* — Studebaker & Brackett PC

(57) ABSTRACT

Provided are an analysis chip and a sample analysis device by which it is possible to perform analysis rapidly and accurately on a plurality of items simultaneously using a small amount of liquid for measurement. An analysis chip (10) is provided with: a substrate (20) formed in a substantially disc shape; an insertion hole (22) formed in the center of the substrate (20), a liquid to be measured being inserted into the insertion hole (22); and micro-flow paths (23) into which the liquid to be measured can be guided from the insertion hole (22) by capillary action, each of the micro-flow paths (23) having therein a plurality of types of antigens (30) that are fixed in place with gaps therebetween, the antigens (30) selectively reacting to components in the liquid to be measured.

8 Claims, 10 Drawing Sheets

10 23 17 23 B 17 23 17 17 18 20 13 23 23 12 23 22 23 23

(51) Int. Cl.

| | |
|---|---|
| ***G01N 37/00*** | (2006.01) |
| ***G01N 35/00*** | (2006.01) |
| ***G01N 35/08*** | (2006.01) |
| ***G01N 21/76*** | (2006.01) |
| ***G01N 33/543*** | (2006.01) |

(52) U.S. Cl.

CPC ....... *G01N 21/76* (2013.01); *G01N 33/54386* (2013.01); *G01N 35/00* (2013.01); *G01N 35/08* (2013.01); *G01N 37/00* (2013.01); *B01L 2200/10* (2013.01); *B01L 2200/12* (2013.01); *B01L 2200/16* (2013.01); *B01L 2300/0609* (2013.01); *B01L 2300/069* (2013.01); *B01L 2300/0803* (2013.01); *B01L 2400/0406* (2013.01); *B01L 2400/0409* (2013.01); *G01N 2201/062* (2013.01)

(56) References Cited

U.S. PATENT DOCUMENTS

| | | | |
|---|---|---|---|
| 6,319,469 | B1 * | 11/2001 | Mian .................. B01F 13/0059 422/63 |
| 2003/0143637 | A1 | 7/2003 | Selvan et al. |
| 2006/0008381 | A1 | 1/2006 | Taguchi et al. |
| 2008/0106577 | A1 | 5/2008 | Hanaoka et al. |
| 2010/0105577 | A1 | 4/2010 | Dugan et al. |
| 2010/0261205 | A1 | 10/2010 | Kakuta et al. |
| 2013/0101993 | A1 * | 4/2013 | Sekizawa .......... B01L 3/502707 435/5 |
| 2013/0302830 | A1 | 11/2013 | Mehra et al. |

FOREIGN PATENT DOCUMENTS

| | | | |
|---|---|---|---|
| JP | H08-062225 | A | 3/1996 |
| JP | 2007-189975 | A | 8/2007 |
| JP | 2008-185504 | A | 8/2008 |
| WO | 90/10875 | A1 | 9/1990 |
| WO | 2007/074756 | A1 | 7/2007 |
| WO | 2012/001972 | A1 | 1/2012 |

OTHER PUBLICATIONS

Extended European Search Report issued by the European Patent Office dated Nov. 22, 2017, which corresponds to EP15792918.3-1553 and is related to U.S. Appl. No. 15/311,132.

* cited by examiner 95
22
20
23
23

ANALYSIS CHIP AND SAMPLE ANALYSIS APPARATUS

TECHNICAL FIELD

The present invention relates to an analysis chip and a sample analysis device used for analyzing target liquid.

BACKGROUND ART

Some sample analysis devices conventionally known analyze liquid itself. Other sample analysis devices conventionally known analyze target liquid prepared by dispersing or dissolving an analysis target, for example, with at least one or more reactants to react with the target liquid being stored in a plurality of storage parts of one reaction container. Patent document 1 discloses a container of this type. The reaction container disclosed in patent document 1 is configured integrally with a plurality of storage parts opened at the upper surface of a substrate and allowing storage of a reagent. Further, at least two of the storage parts are formed independently and configured so as to be capable of communicating with each other.

A sample analysis device requires a constant amount of target liquid for analysis. Meanwhile, if the target liquid is body fluid or blood, etc. to be taken from a living being including a human body, it is preferable that the target liquid be as little as possible in consideration of a burden on a biological body. According to an existing method of conducting analysis using a small amount of target liquid, reaction between a reactant and the target liquid is measured using a micro-flow path into which the target liquid is introduced by means of capillary action. Patent documents 2 and 3 disclose a method or a device using such a micro-flow path. Patent document 2 discloses a nozzle cartridge functioning as a container storing a reagent or an analyte. This nozzle cartridge includes a storage part for a reagent or an analyte, a discharge nozzle, and a flow path through which the reagent or the analyte stored in the storage part is supplied to the discharge nozzle. Patent document 3 discloses a micro chemical chip formed of a first substrate having a sample inlet, a second substrate having a sample flow path, and a third substrate having a sample outlet. The sample inlet is formed as a hole penetrating the first substrate from front to back. The sample flow path is formed as a slit penetrating the second substrate from front to back. The sample outlet is formed as a hole penetrating the third substrate from front to back. The second substrate is arranged between the first and third substrates. The sample inlet and the sample outlet communicate with each other through the sample flow path. The sample flow path is opened on at least one end thereof.

Patent Document 1: Japanese Unexamined Patent Application, Publication No. 2007-189975

Patent Document 2: Japanese Unexamined Patent Application, Publication No. 2008-185504

Patent Document 3: PCT International Publication No. WO2012/001972

DISCLOSURE OF THE INVENTION

Problems to be Solved by the Invention

For measuring a plurality of components in target liquid, reactants corresponding to these components should be stored in a container. In this regard, the configurations disclosed in patent documents 2 and 3 are expected to achieve the effect of restricting the amount of target liquid. However, these configurations still find it difficult to analyze items such as tens of types of items by one measurement.

If the aforementioned method of using an analysis chip with a micro-flow path employs the ELISA (enzyme linked immunosorbent assay) process, for example, target liquid deemed to be no longer necessary during the course of measurement for example of a reaction result or liquid having been used for a different process should be discharged several times from the micro-flow path. Meanwhile, the micro-flow path is a structure using capillary action generated by strong surface tension. Hence, rapidly discharging liquid once introduced into the micro-flow path has not been allowed. Failing to discharge liquid rapidly and properly causes risk of nonuniform reaction time or longer measurement time, etc., which leads to a measurement error. Additionally, conducting measurement of multiple types of items about target liquid takes corresponding longer measurement time. Further improvement has still been desired for a conventional analysis chip and a conventional sample analysis device in terms of conducting analysis of tens of types of items about target liquid by one measurement while restricting the amount of the target liquid.

The present invention is intended to provide an analysis chip and a sample analysis device capable of conducting analysis of a plurality of items rapidly and accurately using a small amount of liquid as a measurement target.

Means for Solving the Problems

The present invention relates to an analysis chip comprising: a substrate formed into a substantially disc shape; an injection port formed at the center of the substrate and through which target liquid as a measurement target is injected; and a flow path that allows introduction of the target liquid into the flow path through the injection port by means of capillary action, wherein multiple types of reactants capable of selectively reacting with a component in the target liquid are fixed to the flow path.

Preferably, the flow path of the analysis chip includes a plurality of flow paths arranged in a radial pattern to extend to an outer edge of the substrate, and the multiple types of reactants capable of selectively reacting with a component in the target liquid are fixed to each of the flow paths to be arranged at given intervals.

Preferably, the analysis chip is formed in such a manner that the flow path surrounds the injection port.

Preferably, the reactants are fixed in the form of spots to the flow path.

Preferably, the reactants fixed to the flow path each have a shape like a thin film having a substantially flat upper surface.

Preferably, the analysis chip further comprises a housing in which the substrate is arranged and housed, and the housing includes: an opening part where an upper surface of the substrate is exposed at least partially; and liquid trapping space provided inside the housing and on an outer peripheral side of the substrate.

Preferably, the analysis chip further comprises an absorber arranged in the liquid trapping space and formed of a member having moisture-retaining properties.

The present invention relates to a sample analysis device comprising: a chip holder that allows installation of the analysis chip on the chip holder; a chip holder rotation mechanism that rotates the chip holder; a pipetting mechanism that injects the target liquid into the injection port of the analysis chip; and a measurement device that allows measurement of reactions between the target liquid and the multiple types of reactants, wherein the target liquid having been introduced into the flow path is discharged by making the chip holder rotation mechanism rotate the chip holder.

Preferably, the chip holder includes a fitting part to make a fit with the analysis chip.

Effects of the Invention

Analysis of a plurality of items about liquid as a measurement target can be conducted rapidly and accurately by the analysis chip and the sample analysis device according to the present invention.

PREFERRED MODE FOR CARRYING OUT THE INVENTION

Figure 1:
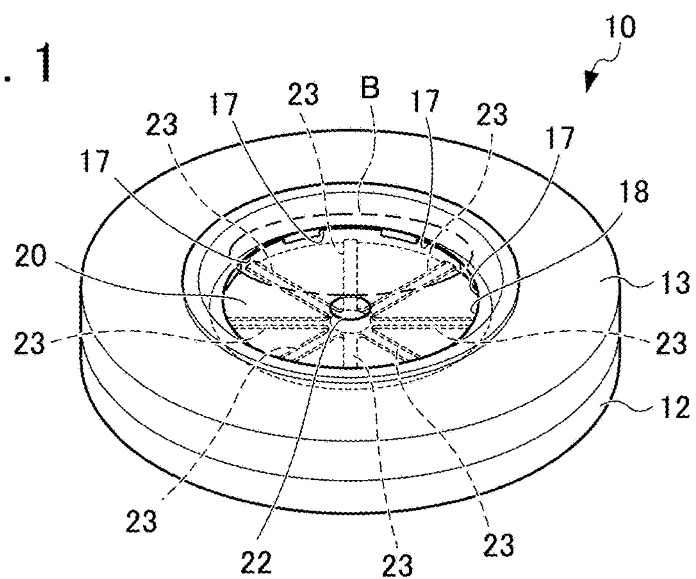
FIG. 1 is a perspective view of an analysis chip according to an embodiment of the present invention.

A preferred embodiment of a biochemical analysis device as a sample analysis device of the present invention and a preferred embodiment of an analysis chip of the present invention are described below by referring to the drawings.

In this embodiment, a biochemical analysis device 50 that determines an allergy of an analyte as target liquid by means of chemiluminescence resulting from antigen-antibody reaction by employing the ELISA process and an analysis chip 10 used in the biochemical analysis device 50 are described as an example of a sample analysis device and an example of an analysis chip of the present invention respectively.

Figure 2:
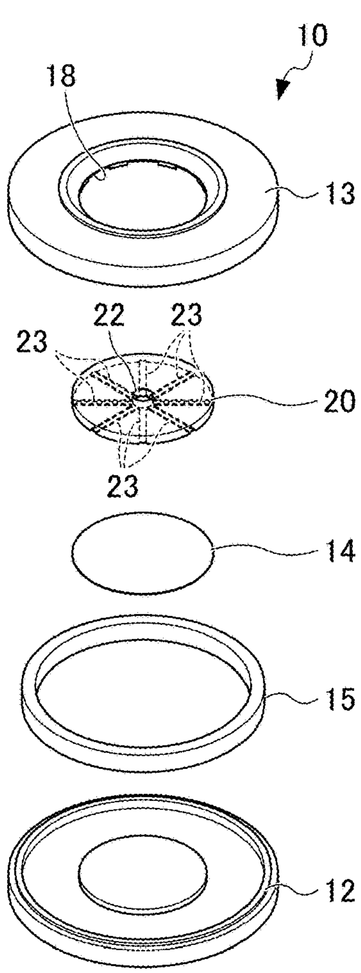
FIG. 2 is a perspective view illustrating the configuration of the analysis chip.
Figure 3:
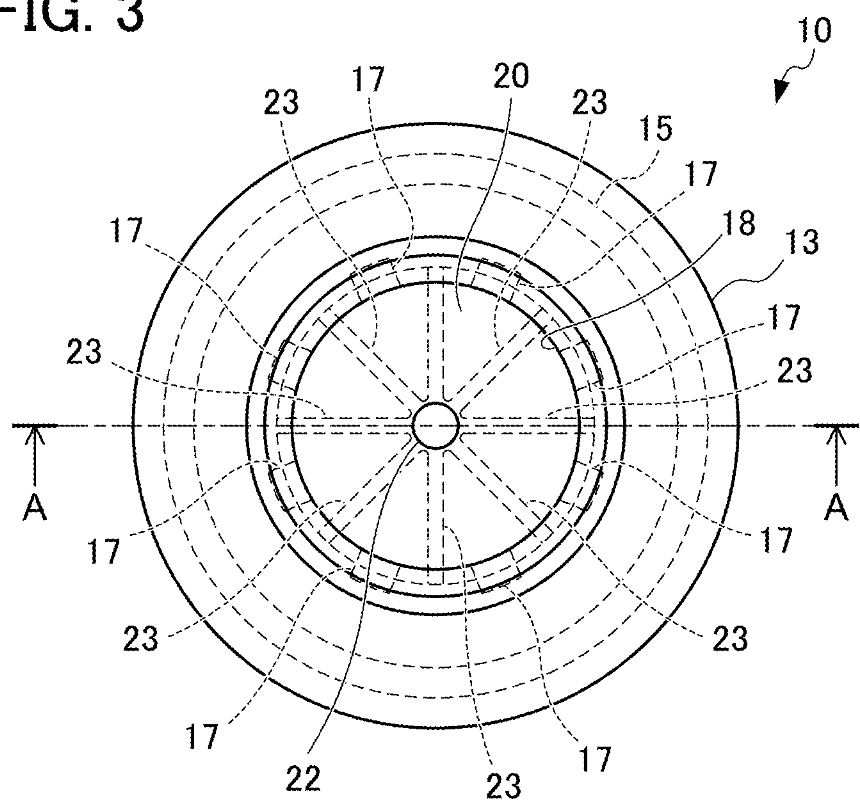
FIG. 3 is a plan view of the analysis chip.
Figure 4:
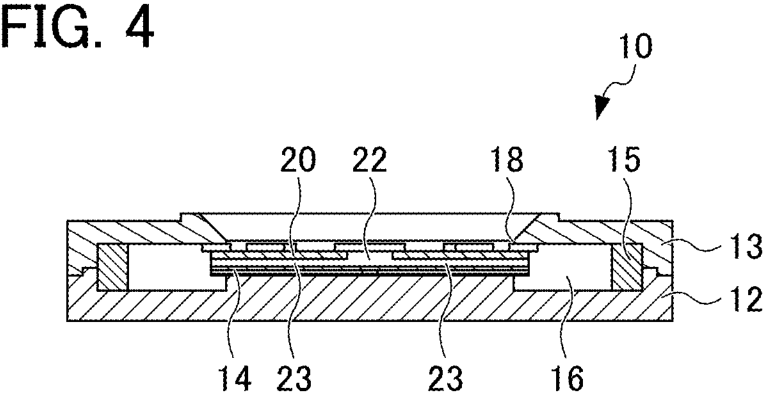
FIG. 4 is a sectional view taken along a line A-A of FIG. 3.
Figure 5:
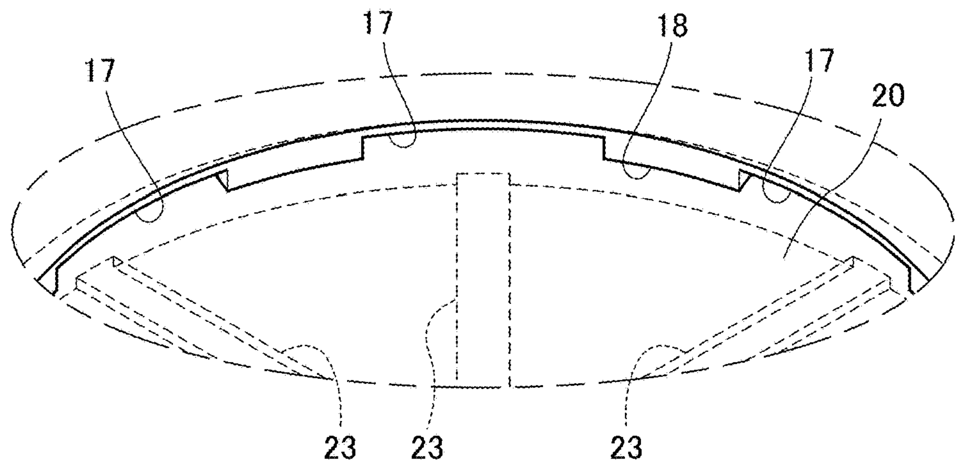
FIG. 5 illustrates a part B of FIG. 1 in an enlarged manner.
Figure 6:
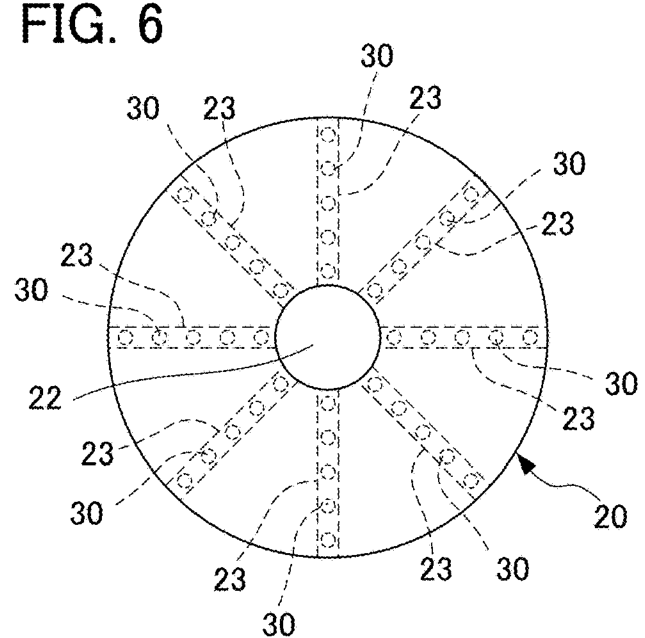
FIG. 6 is a plan view of a substrate schematically illustrating an antigen as a reactant fixed to a micro-flow path.
Figure 7:
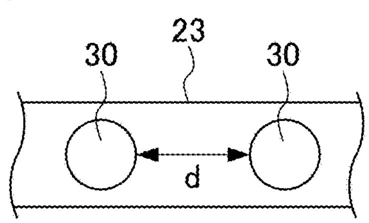
FIG. 7 is an enlarged view schematically illustrating antigens as reactants adjacent to each other in the micro-flow path.

The analysis chip 10 of this embodiment is described. FIG. 1 is a perspective view of the analysis chip 10 according to the embodiment of the present invention. FIG. 2 is a perspective view illustrating the configuration of the analysis chip 10. FIG. 3 is a plan view of the analysis chip 10. FIG. 4 is a sectional view taken along a line A-A of FIG. 3. FIG. 5 illustrates a part B (an area surrounded by a dashed line of FIG. 1) in an enlarged manner. FIG. 6 is a plan view of a substrate schematically illustrating an antigen 30 as a reactant fixed to a micro-flow path 23. FIG. 7 is an enlarged view schematically illustrating antigens 30 as reactants adjacent to each other in the micro-flow path 23.

As illustrated in FIG. 1, the analysis chip 10 of this embodiment has an outer shape formed into a substantially disc shape. As illustrated in FIGS. 2 to 4, the analysis chip 10 includes a substrate 20, a film 14, a lower housing 12, an upper housing 13, an absorber 15, liquid trapping space 16, and an air communication opening 17.

The substrate 20 is formed into a substantially disc shape using a light-transmitting material such as cyclic polyolefin. As illustrated in FIG. 6, the antigen 30 to specifically react with a target substance contained in an analyte (target liquid) as a measurement target is fixed to the substrate 20.

The substrate 20 of this embodiment includes an injection port 22 and a micro-flow path 23. The antigen 30 as a reactant is fixed to the substrate 20.

The substrate 20 is formed into a disc shape. The configuration of the substrate 20 is described. The substrate 20 has a through hole to become the injection port 22. The substrate 20 has a lower surface provided with a plurality of slits equiangularly spaced in a radial pattern with respect to the injection port 22. Each of these slits has one end portion connected to the injection port 22 and an opposite end portion connected to an opening part at an outer edge surface of the substrate 20. The antigen 30 is fixed to the bottom surface of each slit. The film 14 described later is attached to a surface of the substrate 20 provided with the slit. In this way, in this embodiment, the slit formed in the substrate 20 is closed by the film 14 and the slit in the substrate 20 and the film 14 form the micro-flow path 23.

The injection port 22 is used for introducing target liquid such as an analyte or a reagent solution into the micro-flow path 23. The injection port 22 is located at a substantially central position of the substrate 20 formed into a substantially disc shape. The injection port 22 communicates with each of a plurality of micro-flow paths 23 inside the substrate 20.

The micro-flow path 23 is a capillary having one end communicating with the injection port 22 inside the substrate 20 and an opposite end penetrating the substrate 20 to reach as far as an outer edge of the substrate 20 in a radial direction. As illustrated in FIG. 6, the micro-flow path 23 includes a plurality of micro-flow paths 23 extending from the injection port 22 and being equiangularly spaced in a radial pattern. The substrate 20 of this embodiment includes eight micro-flow paths 23.

The micro-flow path 23 is configured in such a manner that liquid is introduced into space inside the micro-flow path 23 by means of capillary action. For example, in this embodiment, based on the viscosity of a blood analyte as target liquid and a result of verification, the micro-flow path 23 is set to have a width of 0.1 mm or more and 3 mm or less and a height of 0.1 mm or more and 0.5 mm or less.

As described above, the antigen 30 is fixed to the inner wall of the micro-flow path 23. The antigen 30 includes a plurality of antigens 30 fixed so as to be aligned linearly in a lengthwise direction of each micro-flow path 23. As illustrated in FIG. 6, the antigens 30 are each fixed in the form of a spot having a diameter smaller than a width between wall surfaces of the micro-flow path 23. The antigens 30 fixed to the wall surfaces of the micro-flow path 23 do not extend over the wall surfaces entirely but they exist as spots on the wall surfaces. By doing so, an area occupied by the fixed antigens 30 can be controlled at a minimum required area. This reduces the probability of contamination or reaction nonuniformity to occur if a large area is occupied by the fixed antigens 30. During measurement of light-emitting reaction described later, fixing the antigens 30 in the form of small-diameter spots as in this embodiment also effectively reduces the probability of interference between light beams resulting from light-emitting reactions generated in adjacent micro-flow paths 23, compared to fixing antigens to the entire region of the micro-flow path 23. In this embodiment, as will also be described later, a camera unit 83 captures an image of an antigen 30 from above where light-emitting reaction is generated, thereby acquiring image information. Thus, light-emitting reaction at one antigen 30 in the form of a small-diameter spot 30 should be assured in a sufficient condition with in-plane uniformity for distinguishing this antigen 30 from a different light-emitting antigen 30 and preventing interference between light beams from these antigens 30. For this purpose, to direct light resulting from light-emitting reaction and to travel toward an image-capturing element mainly in a direction substantially perpendicular to the micro-flow path 23, the upper surface of the antigen 30 in the form of a spot is formed as a substantially smooth surface. This is achieved by controlling the antigen 30 in terms of its viscosity, etc. or forming the antigen 30 by pressing into a smooth shape with a tool such as a stamp, for example.

The antigens 30 are arranged at given intervals. As illustrated in FIG. 7, a distance d between adjacent antigens 30 is set in such a manner that light beams emitted from antigens 30 in adjacent positions do not interfere with each other during measurement of light-emitting reaction. In this embodiment, the adjacent antigens 30 should be formed at positions separated from each other by the distance d that is 60% or more of the diameter of an antigen 30 having a smallest diameter of those of the antigens 30 fixed to the micro-flow path 23.

The antigens 30 are various types of allergens to specifically react with a selected component (target substance) in an analyte. In this embodiment, eight micro-flow paths 23 are formed in the substrate 20. Five antigens 30 are aligned substantially linearly while being separated by the aforementioned given distance d in each of the micro-flow paths 23. To reliably measure reactions of a plurality of antigens 30 fixed to the substrate 20, antigens of the same type may be arranged at a plurality of micro-flow paths or at different positions. Alternatively, antigens of types different from each other may be used. In this case, many pieces of analysis information can be acquired collectively.

The substrate 20 of this embodiment has the aforementioned configuration. The configuration of the substrate 20 is not limited to the aforementioned configuration but can be changed, if appropriate, in a manner that depends on the purpose of the substrate 20. For example, the number of the micro-flow paths 23 may be changed or the micro-flow paths 23 may be arranged at unequal angles. Further, the antigen 30 is described as an example of a reactant fixed to the substrate 20. Alternatively, an antibody may be fixed.

The film 14 is formed into a substantially circular thin-film shape and attached to the lower surface of the substrate 20 as described above. The substrate 20 is arranged over the upper surface of the lower housing 12 through the film 14.

The lower housing 12 is arranged on a lower surface (one surface) side of the substrate 20 and formed into a substantially circular shape having an outer periphery of a larger diameter than the substrate 20. The lower housing 12 is provided with a wall part extending along the outer periphery of the lower housing 12 to form a lower part of the peripheral surface of the analysis chip 10.

The upper housing 13 is arranged on an upper surface (opposite surface) side of the substrate 20. The upper housing 13 is formed into a substantially ring-like shape having an outer periphery of a larger diameter than the substrate 20. The upper housing 13 has an opening part 18 formed at the center of the upper housing 13 and having a circular shape of a smaller diameter than the substrate 20. The upper housing 13 is provided with a wall part extending along the outer periphery of the upper housing 13 to form an upper part of the peripheral surface of the analysis chip 10. A housing of the analysis chip 10 of this embodiment is formed of the lower housing 12 and the upper housing 13.

The absorber 15 is formed of a member having moisture-retaining properties. The absorber 15 is formed into a ring-like shape of a smaller diameter than the lower housing 12 and the upper housing 13 and arranged in the liquid trapping space 16. Liquid having been discharged from the micro-flow path 23 is absorbed by the absorber 15. In the case of biochemical analysis, for example, discharge of liquid targeted for analysis from an analysis device to the outside of a system should strictly be avoided. For this reason, the absorber 15 is provided along the outer periphery of the substrate 20.

As illustrated in FIG. 4, the liquid trapping space 16 is defined by the lower housing 12 and the upper housing 13 into ring-like space surrounding the outer periphery of the substrate 20. An opening part of the micro-flow path 23 on an outer edge side formed in the peripheral surface of the substrate 20 is opened to the liquid trapping space 16. Thus, as will be described later, target liquid discharged from the opening part of the micro-flow path 23 is discharged to the liquid trapping space 16. The target liquid having been discharged to the liquid trapping space 16 is absorbed by the absorber 15 arranged in the liquid trapping space 16. Further, the discharged target liquid achieves the action of moisturizing the liquid trapping space 16 and the micro-flow path 23 in the substrate 20.

As illustrated in FIG. 5, the air communication opening 17 is defined at an inner opening wall of the upper housing 13 by the upper surface of the substrate 20 and the upper housing 13. The air communication opening 17 includes a plurality of air communication openings 17 arranged at substantially regular intervals. As illustrated in FIG. 3, in the radial direction of the substrate 20, the air communication opening 17 is formed slightly inwardly from an opening of the micro-flow path 23 provided at the outer edge of the substrate 20 and close to the liquid trapping space 16. By the presence of the air communication opening 17, the injection port 22 of the substrate 20 and external space communicate with each other through the micro-flow path 23. Thus, air having been injected through the injection port 22 by an air nozzle unit 100 in an air injecting process described later is discharged from the air communication opening 17 to external space through the micro-flow path 23. In the radial direction of the substrate 20, the air communication opening 17 is arranged inwardly from the opening as a liquid discharge opening of the micro-flow path 23 close to the liquid trapping space 16. This prevents liquid discharged from the micro-flow path 23 from being discharged to the outside of the system of the analysis chip 10 through the air communication opening 17.

Figure 8:
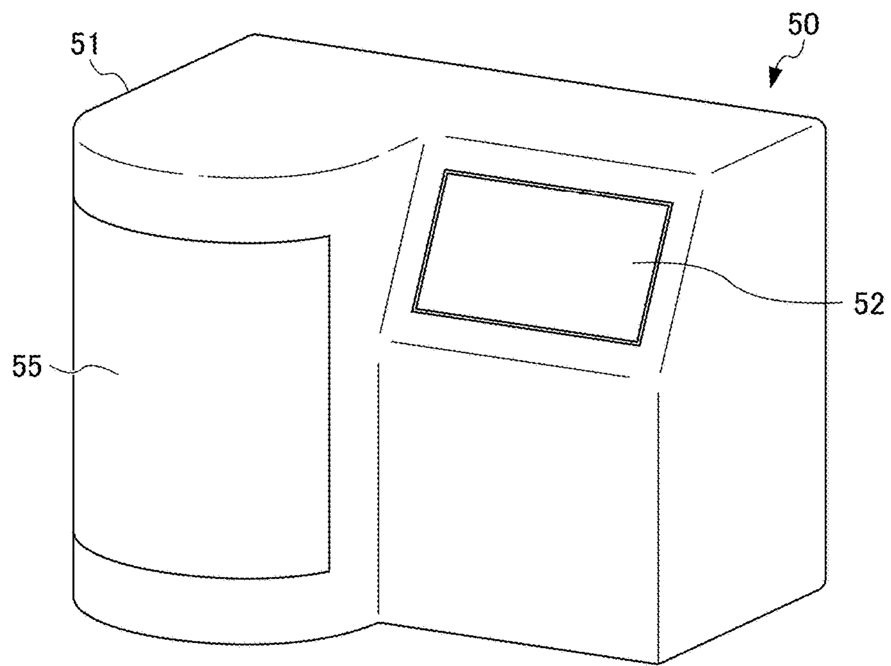
FIG. 8 is a perspective view of a biochemical analysis device according to the embodiment of the present invention.
Figure 9:
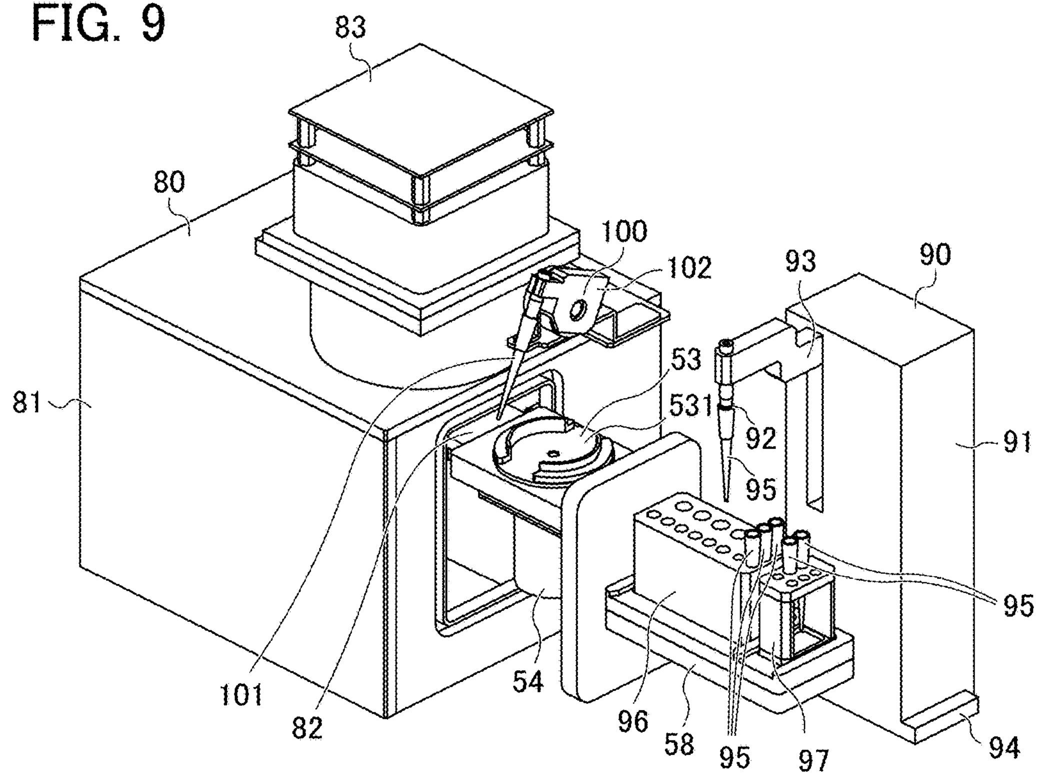
FIG. 9 is a perspective view illustrating the inside of the biochemical analysis device in outline.
Figure 10:
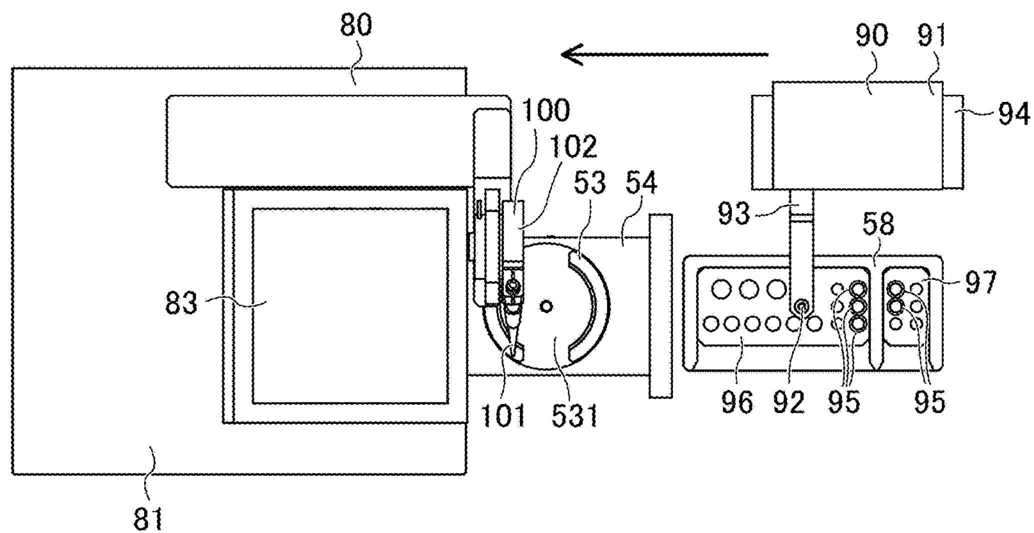
FIG. 10 is a plan view illustrating the inside of the biochemical analysis device in outline.
Figure 11:
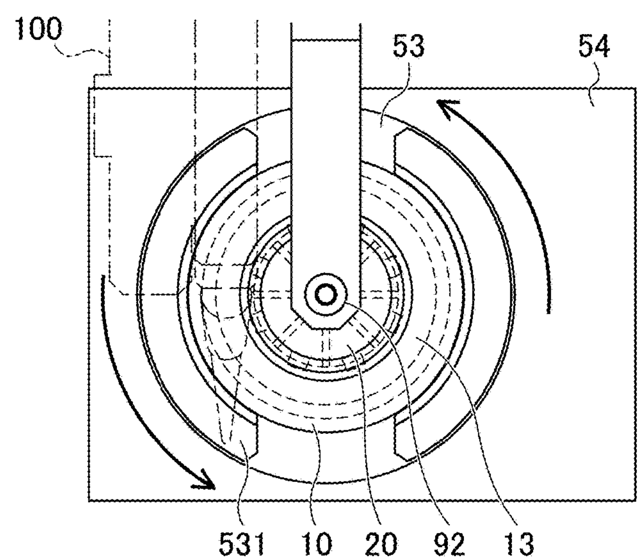
FIG. 11 is a plan view of a chip holder illustrating a state where a pipetting unit is injecting target liquid into the analysis chip.
Figure 12:
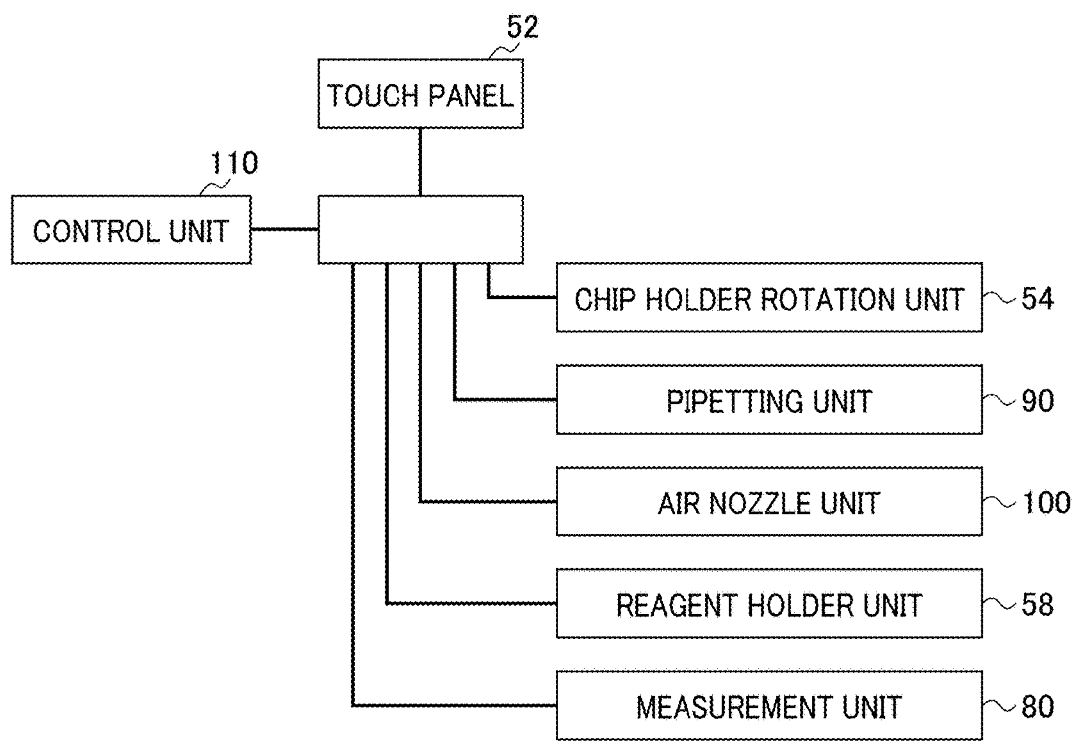
FIG. 12 is a block diagram schematically illustrating a relationship between a control unit and each structure.
Figure 13:
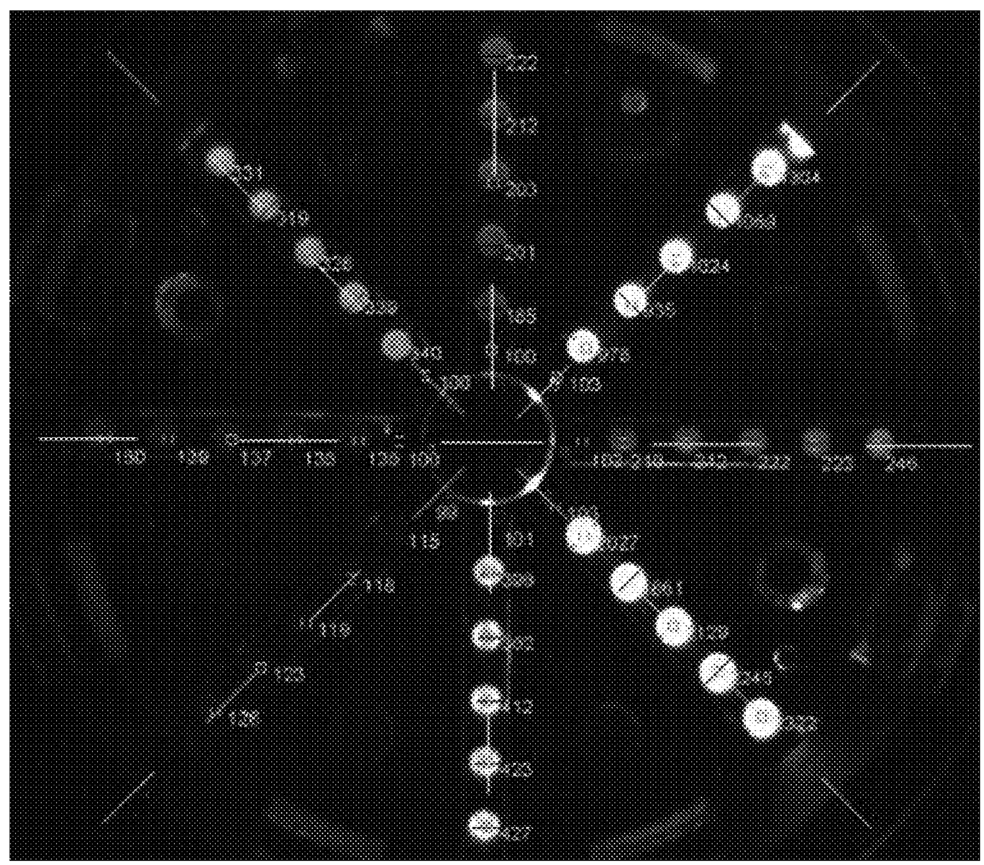
FIG. 13 illustrates an example of analysis image information acquired by a measurement unit.

The analysis chip 10 of this embodiment has the aforementioned configuration. The following description is about the biochemical analysis device 50 that analyzes target liquid using the analysis chip 10 of this embodiment. FIG. 8 is a perspective view of the biochemical analysis device 50 according to the embodiment of the present invention. FIG. 9 is a perspective view illustrating the inside of the biochemical analysis device 50 in outline. FIG. 10 is a plan view illustrating the inside of the biochemical analysis device 50 in outline. FIG. 11 is a plan view of a chip holder 53 illustrating a state where a pipetting unit 90 is injecting target liquid into the analysis chip 10. FIG. 12 is a block diagram schematically illustrating a relationship between a control unit 110 and each structure. FIG. 13 illustrates an example of analysis image information acquired by a measurement unit 80.

As illustrated from FIGS. 8 to 12, the biochemical analysis device 50 includes a housing 51, a touch panel 52, a chip holder rotation unit 54, the measurement unit 80, the pipetting unit 90, the air nozzle unit 100, a reagent holder unit 58, and the control unit 110.

The housing 51 houses each structure of the biochemical analysis device 50 and separates internal mechanisms for analysis and external space. The housing 51 is provided with a door 55.

The touch panel 52 functions both as operation means and display means of the biochemical analysis device 50. The touch panel 52 is used for making various settings and performing various operations, and for displaying a measurement result and an analysis result, for example.

The chip holder rotation unit 54 rotates the analysis chip 10. In this embodiment, an injecting process of injecting target liquid into the analysis chip 10 and a discharging process for liquid having been introduced into the micro-flow path 23 are performed by making the chip holder rotation unit 54 rotate the analysis chip 10. The configuration of the chip holder rotation unit 54 is described below.

The chip holder rotation unit 54 of this embodiment includes the chip holder 53, a chip holder drive motor, a temperature adjustment unit, and a temperature sensor.

The chip holder 53 is installed at an upper part of the chip holder rotation unit 54. The chip holder 53 includes a fitting part 531 to make a fit with the analysis chip 10. The fitting part 531 is formed at the upper surface of the chip holder 53 and functions as a frame part to contact a portion of the peripheral surface of the analysis chip 10. As illustrated in FIG. 11, with the analysis chip 10 placed at the chip holder 53, the fitting part 531 holds a portion of the outer periphery of the analysis chip 10 to prevent falling off of the analysis chip 10 from the chip holder 53 to be caused by centrifugal force.

The fitting part 531 is configured to make a fit with the analysis chip 10 in such a manner that the center of the injection port 22 of the analysis chip 10 and the center of rotation of the chip holder 53 substantially agree with each other. The analysis chip 10 is configured to be placed in a substantially horizontal posture while being installed at the chip holder 53.

The analysis chip 10 and the fitting part 531 can also be configured as follows. An analysis chip fitting part with a protrusion, a recess, or a protrusion and a recess is formed at the lower surface of the analysis chip 10 (lower surface of the lower housing 12). Then, a shape conforming to the shape of the analysis chip fitting part is formed at a surface of the fitting part 531 to contact the lower surface of the analysis chip 10. This can make a fit between the analysis chip 10 and the fitting part 531 more reliably, while making it possible to adjust the rotation speed of the analysis chip 10 more properly. Additionally, as a result of increase in the area of contact between the analysis chip 10 and the fitting part 531, heat of the analysis chip 10 can be adjusted more easily by the temperature adjustment unit through the chip holder 53 in an incubation process described later, thereby achieving efficient temperature adjustment. In consideration of expansion or compression of the chip holder 53 by heat during incubation, the shapes formed at the analysis chip fitting part and the fitting part 531 may be shapes that can be detached from each other easily such as a mountain shape and a valley shape, teeth-like shapes, conical shapes, or corrugated shapes, for example.

The chip holder drive motor is arranged inside the chip holder rotation unit 54 and has a drive shaft coupled to the rotary shaft of the chip holder 53 (not illustrated in the drawings). The chip holder drive motor is configured to rotate at a frequency that can be adjusted at any value. The chip holder rotation unit 54 is electrically connected to the control unit 110. Based on a signal from the control unit 110, the chip holder rotation unit 54 adjusts the rotation frequency of the chip holder drive motor to rotate the chip holder 53 at a given speed. In this embodiment, the chip holder 53 is configured to rotate at a speed that can be switched between an injection rotation speed described later and a liquid discharge speed described later.

The injection rotation speed is a rotation speed of the chip holder 53 employed when the pipetting unit 90 injects liquid into the injection port 22 of the analysis chip 10.

The liquid discharge speed is a rotation speed employed when liquid having been introduced into the micro-flow path 23 of the analysis chip 10 is discharged from the micro-flow path 23 to the liquid trapping space 16. To discharge liquid from the micro-flow path 23 by means of centrifugal force, the liquid discharge speed of this embodiment is set so as to rotate the chip holder 53 at a speed higher than the injection rotation speed that does not cause discharge of liquid having been introduced into the micro-flow path 23.

The temperature adjustment unit is arranged inside the chip holder rotation unit 54 and configured to achieve temperature adjustment of the analysis chip 10 installed at the chip holder 53 (not illustrated in the drawings). By the presence of the temperature adjustment unit, pre-incubation and incubation for generating reaction between the antigen 30 and target liquid proceed properly.

The temperature sensor is arranged inside the chip holder rotation unit 54 (not illustrated in the drawings). Temperature information acquired by the temperature sensor is transmitted to the control unit 110. The control unit 110 is configured in such a manner that the control unit 110 can adjust warming by the temperature adjustment unit based on the acquired temperature information.

The measurement unit 80 is described next. The measurement unit 80 measures light-emitting reaction. The measurement unit 80 includes a dark box 81, a chip holder movement mechanism 82, the camera unit 83, and an LED unit.

The dark box 81 is configured as a hermetically-sealed rectangular parallelepiped. The dark box 81 functions as a dark box for shielding light from the outside of the system during measurement and as a temperature adjusting chamber for heat retention during pre-incubation and incubation. The dark box 81 has an opening part at one side surface.

The chip holder movement mechanism 82 includes drive means (not illustrated in the drawings) arranged at the opening part of the dark box 81 and used for moving the chip holder rotation unit 54. The chip holder movement mechanism 82 allows the chip holder rotation unit 54 to move between a liquid injection position, an air injection position, and a measurement position.

The liquid injection position of the chip holder rotation unit 54 is a position employed when the pipetting unit 90 injects liquid into the analysis chip 10. The chip holder rotation unit 54 at the liquid injection position is arranged outside the dark box 81 (in the state of FIGS. 9 and 10). The air injection position of the chip holder rotation unit 54 is a position employed when the air nozzle unit 100 injects air into the analysis chip 10.

The measurement position of the chip holder rotation unit 54 is a position employed when the measurement unit 80 measures the analysis chip 10 inside the dark box 81. The measurement position is such that the opening part of the dark box 81 is closed in response to movement of the chip holder rotation unit 54 to hermetically seal the dark box 81.

The camera unit 83 is arranged above the dark box 81. The camera unit 83 is a measurement unit (image capturing unit) to capture an image of the analysis chip 10 from above at the measurement position. Various determinations are made based on image information resulting from image capturing by the camera unit 83. The exposure time of the camera unit 83 of this embodiment is adjusted based on an experimental result, etc., so as to allow detection of emission of very weak light. A member for reducing influence of reflected light such as a polarizing plate may be arranged inside the dark box 81.

The measurement unit 80 makes the camera unit 83 capture an image of the analysis chip 10 at the measurement position where light-emitting reaction is generated, thereby acquiring image information as measurement information. As illustrated in FIG. 13, the camera unit 83 acquires information about an image with a resolution by which the position of light-emitting reaction can be identified clearly. The camera unit 83 includes the LED unit.

The LED unit is an illumination device for illuminating the inside of the dark box 81 during image capturing by the camera unit 83.

The measurement unit 80 is electrically connected to the control unit 110. The chip holder movement mechanism 82, the camera unit 83, the LED unit, and the temperature sensor of the measurement unit 80 are configured in such a manner as to allow transmission and receipt of various signals to and from the control unit 110. Based on a signal from the control unit 110, the measurement unit 80 drives the drive means of the chip holder movement mechanism 82 so as to move the chip holder rotation unit 54 to the liquid injection position, the air injection position, or the measurement position. A signal from the control unit 110 is also used for making the camera unit 83 capture an image or for control over luminosity adjustment by the LED unit, etc.

The pipetting unit 90 is described next. The pipetting unit 90 pipettes liquid (target liquid) into the injection port 22 of the analysis chip 10 placed at the chip holder 53. Liquid to be injected into the analysis chip 10 by the pipetting unit 90 includes a blocking solution, an analyte, a cleaning liquid, and a luminescent substrate, for example.

The pipetting unit 90 includes a pipetting casing 91, a pipetting nozzle 92, a pipetting nozzle movement mechanism 93, and a pipetting unit movement mechanism 94.

A detachable pipette chip 95 is attached to the pipetting nozzle 92. Liquid is pipetted into the analysis chip 10 using the pipette chip 95 as a tip portion of the pipetting nozzle 92. The pipetting nozzle movement mechanism 93 moves the pipetting nozzle 92 in a vertical direction. The pipetting unit movement mechanism 94 moves the pipetting unit 90. The pipetting unit 90 can be moved in a horizontal direction by the pipetting unit movement mechanism 94. The pipetting unit 90 can move between a liquid injection position illustrated in FIG. 11 where the pipetting unit 90 is close to the chip holder 53, and a standby position illustrated in FIG. 10 where the pipetting unit 90 is separated from the chip holder 53.

The pipetting unit 90 moves the pipetting nozzle 92 between a pipette chip attachment position, a pipette chip detachment position, the standby position, and the liquid injection position by using the pipetting nozzle movement mechanism 93 and the pipetting unit movement mechanism 94. In the pipetting unit 90, based on a signal from the control unit 110, drive means of each of the pipetting nozzle movement mechanism 93 and the pipetting unit movement mechanism 94 is driven so as to move the pipetting nozzle 92 to the liquid injection position, the pipette chip attachment position, the pipette chip detachment position, or the standby position.

The pipette chip attachment position of the pipetting unit 90 is a position employed for attaching an unused pipette chip 95 to be placed in the reagent holder unit 58 described later. The pipette chip detachment position of the pipetting unit 90 is a position employed when a used pipette chip 95 is detached from the pipetting nozzle 92 by a pipette chip detachment mechanism (not illustrated in the drawings) of the reagent holder unit 58. The standby position is the position of the pipetting nozzle 92 employed while the pipetting unit 90 is moving. The standby position is higher than any of the liquid injection position, the pipette chip attachment position, and the pipette chip detachment position. The pipetting nozzle 92 is at the standby position while the pipetting unit 90 is moving to cause no interference with movement of the pipetting nozzle 92.

The liquid injection position of the pipetting unit 90 is a position employed for injection of liquid into the analysis chip 10. The liquid injection position of this embodiment is set in such a manner that the tip of the pipette chip 95 installed at the tip of the pipetting nozzle 92 substantially agrees with the center of rotation of the chip holder 53 in a plan view.

The liquid injection position of this embodiment is set in such a manner that the tip of the pipette chip 95 is placed at a position below the upper surface of the substrate 20 and not contacting the bottom surface of the injection port 22.

An injecting process at the liquid injection position is performed while the chip holder 53 rotates at the injection rotation speed. The pipetting unit 90 injects liquid into the analysis chip 10 continuously at a constant speed or in stages. The tip of the pipette chip 95 is placed below the upper surface of the substrate 20. This prevents flying-off of liquid over the upper surface of the substrate 20 or blockage of the injection port 22 with droplets of target liquid. As a result, the target liquid of a minute amount can be introduced rapidly and properly into the micro-flow path 23 through the injection port 22.

As a result of pipetting while rotating the chip holder 53, even if a tip portion of the pipette chip 95 deviates from the center of rotation, distances from the tip portion of the pipette chip 95 to a plurality of the micro-flow paths 23 can be substantially equal. Thus, liquid is introduced into these micro-flow paths 23 with substantially equal probability. This prevents the occurrence of a problem such as failing to introduce liquid properly into some of these micro-flow paths 23. This can effectively reduce influence on the injecting process to be exerted by the accuracy of the shape or attachment condition of the tip portion of the pipetting nozzle 92, particularly in the case where the tip portion of the pipetting nozzle 92 is formed of a disposable pipette chip 95, for example.

A method of injecting liquid into the analysis chip 10 using the pipetting unit 90 can be determined properly in a manner that depends on the amount of the liquid to be injected. For example, to reduce time of the injection, without injecting the liquid in stages, a given amount of the liquid may be injected at a time. Alternatively, a speed of the injection may be changed.

The air nozzle unit 100 is described next. The air nozzle unit 100 is for auxiliary discharge of liquid with air to the liquid trapping space 16 remaining in the micro-flow path 23 of the analysis chip 10 without having been discharged only by centrifugal force resulting from rotation. The air nozzle unit 100 is arranged above the chip holder rotation unit 54.

The air nozzle unit 100 includes an air nozzle 101 and an air nozzle movement mechanism 102. In this embodiment, the air nozzle unit 100 injects air while the chip holder 53 is rotated at the liquid discharge speed.

The air nozzle movement mechanism 102 moves the air nozzle 101 between an air injection position and a standby position. The air nozzle 101 is moved between the air injection position and the standby position by the air nozzle movement mechanism 102.

The air injection position is a position employed for injection of air into the injection port 22 of the analysis chip 10. A tip portion of the air nozzle 101 at the air injection position faces the injection port 22 of the analysis chip 10. In this embodiment, the standby position is a position employed when the air nozzle unit 100 does not inject air. When the air nozzle 101 is at the standby position, the tip portion of the air nozzle 101 is placed above the air injection position and does not face the injection port 22.

At the air injection position, air is injected while the chip holder 53 rotates at the liquid discharge speed. Inside the analysis chip 10, liquid remaining in the micro-flow path 23 is discharged to the liquid trapping space 16 with air injected through the injection port 22. Even if liquid remains in the micro-flow path 23 by means of capillary action, such remaining liquid can reliably be removed from the micro-flow path 23 with the air injected from the air nozzle unit 100. The liquid having been discharged to the liquid trapping space 16 is absorbed by the absorber 15. The air having exited the micro-flow path 23 passes through the air communication opening 17 to be discharged to the outside the system of the analysis chip 10. As described above, in the analysis chip 10, the air communication opening 17 is arranged inwardly in the radial direction from the exit of the micro-flow path 23, as illustrated in FIG. 3. This prevents the liquid discharged from the micro-flow path 23 from being discharged to the outside of the system of the analysis chip 10 through the air communication opening 17, while allowing discharge of the air to the outside of the system of the analysis chip 10.

In this embodiment, air is injected after rotation of the chip holder 53 is started. By doing so, most of liquid is discharged in advance by centrifugal force from the micro-flow path 23 and thereafter, air is injected. If liquid is discharged only by means of air injection, discharge of the liquid from a particular micro-flow path 23 may be finished first. In this case, air may exist intensively only in a discharge channel in this micro-flow path 23, thus possibly failing to discharge the liquid from remaining micro-flow paths. Such a problem can be avoided by discharging most of the liquid in advance by means of centrifugal force resulting from rotation of the chip holder 53. In this way, according to the configuration of this embodiment, every liquid in the plurality of micro-flow paths 23 can efficiently be discharged.

The reagent holder unit 58 is described next. The reagent holder unit 58 is for installation of a reagent cartridge 96 and the pipette chip 95 on the reagent holder unit 58.

The reagent cartridge 96 stores multiple types of target liquid to be injected into the analysis chip 10 including a blocking solution, an analyte, a luminescent substrate, a cleaning liquid, etc. A plurality of unused pipette chips 95 is placed in the reagent cartridge 96. The reagent holder unit 58 of this embodiment includes an installation part (not illustrated in the drawings) with which the reagent cartridge 96 can be attached and detached. The reagent cartridge 96 is fixed to the installation part.

The pipette chip 95 is attached to the pipetting nozzle 92 of the pipetting unit 90. The pipette chip 95 is a disposable chip to be changed for each liquid to be injected. The reagent holder unit 58 of this embodiment includes a disposal housing part 97 for housing a used pipette chip 95 and the pipette chip detachment mechanism (not illustrated in the drawings). The pipette chip detachment mechanism detaches a used pipette chip 95 from the pipetting nozzle 92.

The control unit 110 is described next. The control unit 110 is a computer formed of a CPU, a memory as a storage, etc. As illustrated in FIG. 12, the control unit 110 is electrically connected to the touch panel 52, the chip holder rotation unit 54, the measurement unit 80, the pipetting unit 90, the air nozzle unit 100, etc. As described above, each unit performs all of or some of its operations in response to a signal from the control unit 110. Specifically, a signal from the control unit 110 is used for controlling a sequence of the biochemical analysis device 50, etc. that includes control over rotation speed of the chip holder 53, movement of the chip holder rotation unit 54, movement of the pipetting unit 90 and a pipetting process by the pipetting unit 90, air injection by the air nozzle unit 100, image capturing by the measurement unit 80, and warming by the temperature adjustment unit, for example. The control unit 110 is further responsible for image processing, setting and storage of a test condition, output of analysis data, etc. Exerting control over the measurement unit 80 by the control unit 110 includes exerting control over all the structures of the measurement unit 80 including the camera unit 83, the chip holder movement mechanism 82, and the LED unit. Additionally, exerting control over the chip holder rotation unit 54, the pipetting unit 90, the air nozzle unit 100, and the reagent holder unit 58 includes exerting control over the movement mechanism of each of these structures.

In this embodiment, as described above, antigen-antibody reaction is measured based on image information acquired as a result of capturing of an image by the camera unit 83 about light-emitting reaction generated at the measurement position.

Specificity of reaction with a selected substance is acquired from an antigen 30 exhibiting this light-emitting reaction in the acquired image information. Information for example about the intensity of the reaction specificity is acquired based on the intensity of the emitted light.

Figure 14:
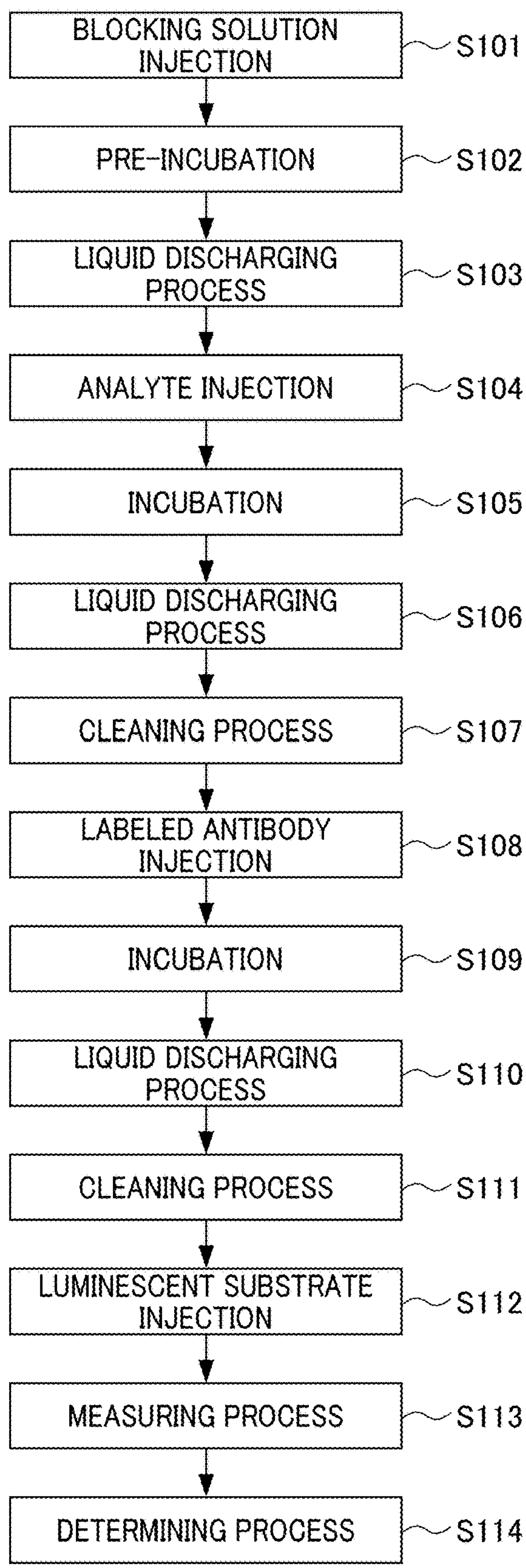
FIG. 14 is a flowchart of measurement and analysis conducted by the biochemical analysis device according to the embodiment of the present invention.

The biochemical analysis device 50 of this embodiment has the aforementioned configuration. A flow of measurement by the biochemical analysis device 50 of this embodiment is described next. FIG. 14 is a flowchart of measurement and analysis conducted by the biochemical analysis device 50 according to the embodiment of the present invention.

A user of the biochemical analysis device 50 is placed the analysis chip 10 at the chip holder 53. Further, the user places the reagent cartridge 94 storing an analyte, a reagent solution, a cleaning liquid, the pipette chip 95, etc. at the reagent holder unit 58. Next, the user operates the touch panel 52 to start measurement at the biochemical analysis device 50. In response to receipt of a signal indicating start of the measurement from the touch panel 52, the control unit 110 starts control over sequential steps from blocking solution injection in step S101.

First, the blocking solution injection (S101) is performed to prevent non-specific adsorption of an antibody, etc. to a part in the micro-flow path 23 other than the antigen 30. The blocking solution injection (S101) is performed by making the pipetting unit 90 inject a blocking solution through the injection port 22 of the analysis chip 10 while the chip holder 53 is rotated at the injection rotation speed. The blocking solution having been injected through the injection port 22 is introduced into the plurality of micro-flow paths 23 formed in a radial pattern with respect to the injection port 22 to extend over the micro-flow paths 23 entirely by means of the aforementioned capillary action. After the pipette chip 95 is detached, a pre-incubation process (S102) is performed to fix the injected blocking solution sufficiently to a part in the micro-flow path 23 other than the antigen 30.

The pre-incubation process (S102) is performed with the chip holder 53 having been moved to the inside of the dark box 81 functioning as a temperature adjusting chamber. After the pre-incubation process (S102) is performed for a given period of time, the chip holder 53 is returned to a position outside the dark box 81. Then, for analyte injection (S104), a liquid discharging process (S103) is performed to discharge the blocking solution to the outside of the micro-flow path 23 to release the inside of the micro-flow path 23.

The liquid discharging process (S103) is performed by making the chip holder rotation unit 54 rotate the chip holder 53 at the liquid discharge speed and making the air nozzle unit 100 inject air through the injection port 22 of the analysis chip 10.

The micro-flow path 23 is formed to extend in a direction toward its outer edge from the center of rotation. The remaining blocking solution is moved and discharged to the liquid trapping space 16 outside the outer edge of the micro-flow path 23 by centrifugal force, while being discharged further with air substantially reliably to the liquid trapping space 16. As described above, even in the micro-flow path 23 where strong surface tension is generated by capillary action, the liquid discharging process can still be performed rapidly and effectively.

The blocking solution having been discharged from the micro-flow path 23 is absorbed by the absorber 15 in the liquid trapping space 16. According to the analysis chip 10 of this embodiment, liquid having been discharged from the micro-flow path 23 is absorbed by the absorber 15 provided in the liquid trapping space 16. This can reliably prevent discharge of target liquid to the outside of the system of the analysis chip 10. The target liquid having been discharged to the liquid trapping space 16 is absorbed by the absorber 15. This prevents the target liquid having been discharged from the micro-flow path 23 from flowing back into the micro-flow path 23, so that subsequent processes are performed properly.

The analyte injection (S104) is performed by injecting an analyte into the analysis chip 10 while the chip holder 53 is rotated at the injection rotation speed. Like in the blocking solution injection (S101), the analyte having been injected through the injection port 22 is introduced uniformly into the plurality of micro-flow paths 23 by means of capillary action. After the analyte injection (S104), an incubation process (S105) is performed to prompt antigen-antibody reaction between the antigen 30 and the analyte.

Like the pre-incubation process (S102), the incubation process (S105) is performed with the chip holder 53 having been moved to the inside of the dark box 81 functioning as a temperature adjusting chamber. The incubation is performed by making temperature adjustment for a given period of time using the temperature adjustment unit.

The absorber 15 of the analysis chip 10 contains the blocking solution already absorbed as a result of the liquid discharging process for the blocking solution (S103), so that the inside of the analysis chip 10 has already been humidified. This prevents drying of the inside of the micro-flow path 23 during the incubation (S105). Then, the chip holder 53 is taken out of the dark box 81 to proceed to a liquid discharging process for the analyte (S106).

Like the liquid discharging process for the blocking solution (S103), the liquid discharging process for the analyte (S106) is performed by rotating the chip holder 53 at the liquid discharge speed and making the air nozzle unit 100 inject air. As a result of this liquid discharging process (S106), the analyte in the micro-flow path 23 is discharged to the liquid trapping space 16 and absorbed by the absorber 15. After the inside of the micro-flow path 23 is released by this liquid discharging process for the analyte, a cleaning process (S107) is performed.

Like the blocking solution injection (S101), the cleaning process (S107) is performed by rotating the chip holder 53 at the injection rotation speed and injecting a cleaning liquid through the injection port 22 of the analysis chip 10 and introducing the cleaning liquid into the plurality of micro-flow paths 23 formed in a radial pattern with respect to the injection port 22. Next, like the liquid discharging process for the blocking solution (S103), a liquid discharging process for the cleaning liquid is performed by making the chip holder rotation unit 54 rotate the chip holder 53 at the liquid discharge speed and making the air nozzle unit 100 inject air. By performing the aforementioned cleaning process of injecting and discharging the cleaning liquid, the liquid remaining in the plurality of micro-flow paths 23 of the substrate 20 is discharged together with the cleaning liquid. The cleaning liquid is also absorbed by the absorber 15 provided in the liquid trapping space 16. After the cleaning process (S107), labeled antibody injection (S108) of deriving a luminescent substrate by means of enzyme reaction is performed. The luminescent substrate is used for a final process of measuring light emission and to be added to the antigen 30 where the antigen-antibody reaction is generated by the incubation (S105).

Like the blocking solution injection (S101), the analyte injection (S104), or the cleaning liquid injection (S107), the labeled antibody injection (S108) is performed by injecting a labeled antibody and rotating the chip holder 53 at the injection rotation speed. Like the incubation (S105) performed to prompt antigen-antibody reaction, incubation (S109) is performed after the injection of the labeled antibody to add the labeled antibody reliably to the antigen 30 where the antigen-antibody reaction is generated. Next, a liquid discharging process for the labeled antibody (S110) is performed.

A cleaning process for the labeled antibody (S111) is similar to the cleaning process in step S107 and is performed by injecting and discharging a cleaning liquid. The cleaning process (S111) including injection and discharge of the cleaning liquid is repeated several times, where necessary, thereby obtaining reliable cleaning effect. After the cleaning process (S111), a process of luminescent substrate injection (S112) is performed.

Like the blocking solution injection (S101), the analyte injection (S104), or the cleaning liquid injection (S107), the luminescent substrate injection (S112) is performed by injecting the luminescent substrate into the chip holder 53 rotated at the injection rotation speed. After the luminescent substrate injection (S112), a measuring process (S113) is performed.

The measuring process (S113) is performed by making the camera unit 83 of the measurement unit 80 capture an image of the analysis chip 10. The presence or absence of light emission and the intensity of the emitted light at each antigen 30 indicating a result of the measurement can be displayed for example on the touch panel 52, stored in the storage of the control unit 110, transmitted to an external computer connected through wired or wireless communication, or output from an output device such as a printer.

A determining process (S114) is performed on all types of antigens 30 (in this embodiment, 40 types). In the determining process (S114), based on the type of the antigen 30 generating light-emitting reaction understood from a result of the measurement obtained in the measuring process (S113), specificity of reaction of the analyte with each antigen 30 is determined and the intensity of the reaction specificity is determined based on the intensity of the emitted light. As described above, the analysis chip 10 and the biochemical analysis device 50 according to this embodiment achieve measurement of a large number of items of as many as 40 types collectively and simultaneously within a short length of time.

The analysis chip 10 of this embodiment described above achieves the following effects.

The analysis chip 10 of this embodiment includes: the substrate 20 formed into a substantially disc shape; the injection port 22 formed at the center of the substrate 20 and through which target liquid as a measurement target is injected; and the plurality of micro-flow paths 23 formed in a radial pattern to extend from the injection port 22 to the outer edge of the substrate 20 and allowing introduction of the target liquid into the micro-flow paths 23 by means of capillary action. Multiple types of antigens 30 to selectively react with a component in the target liquid are fixed to each of the micro-flow paths 23 to be spaced from each other. In this way, multiple types of antigens 30 are fixed to one micro-flow path 23. This makes it possible to make measurement of a plurality of items at a time, while restricting a required amount of the target liquid. Additionally, by forming the micro-flow paths 23 in a radial pattern, the target liquid remaining in the micro-flow paths 23 can be discharged from the micro-flow paths 23 by means of centrifugal force. This works effectively, particularly in sample analysis of repeating processes of injecting and discharging multiple types of liquid several times during the course of measurement, like in this embodiment.

In the analysis chip 10, the antigen 30 is fixed in the form of a spot to the micro-flow path 23. This makes it possible to arrange a large number of antigens 30 in a limited area.

In the analysis chip 10, the antigen 30 fixed to the micro-flow path 23 has a shape like a thin film having a flat upper surface. By doing so, for acquiring image information by making the camera unit 83 capture an image of the analysis chip 10 from above, the upper surface of the antigen 30 is formed so as to direct light (optical axis) resulting from light-emitting reaction mainly in a direction substantially perpendicular to the micro-flow path 23. This prevents interference with a different light-emitting antigen 30, so that an image of light-emitting reaction can favorably be captured.

The analysis chip 10 further includes a housing in which the substrate 20 is arranged and housed and formed of the lower housing 12 and the upper housing 13. The housing includes the opening part 18 where the upper surface of the substrate 20 is exposed at least partially, and the liquid trapping space 16 provided inside the housing and on an outer peripheral side of the substrate 20. This prevents target liquid having been discharged from the micro-flow path 23 from being discharged to the outside of the system of the analysis chip 10 at the liquid trapping space 16 inside the housing, while allowing injection of liquid through the opening part 18 from above the substrate 20 and allowing image capturing by the camera unit 83. The forgoing can be rephrased as follows. The analysis chip 10 of this embodiment further includes: the lower housing 12 formed into a larger diameter than the substrate 20; the upper housing 13 having the opening part 18 and being formed into a larger diameter than the substrate 20; and the liquid trapping space 16 formed on the outer peripheral side of the substrate 20 using the lower housing 12 and the upper housing 13. Thus, target liquid having been discharged from the micro-flow path 23 is trapped in the liquid trapping space 16, so that the target liquid can be prevented from flowing out of the analysis chip 10. This works effectively, particularly in the biochemical analysis device 50 required to avoid diffusion or leakage of an analyte taken from a biological body into and out of the biochemical analysis device 50.

The analysis chip 10 further includes the absorber 15 arranged in the liquid trapping space 16 and formed of a member having moisture-retaining properties. Thus, target liquid having been discharged to the liquid trapping space 16 is absorbed by the absorber 15. This achieves the action of moisturizing the liquid trapping space 16 and the micro-flow path 23 in the substrate 20, while preventing the target liquid having been discharged from the micro-flow path 23 from flowing back into the micro-flow path 23.

The analysis chip 10 includes the air communication opening 17 formed around the opening part 18 and between the upper surface (surface close to the opening part 18) of the substrate 20 and the upper housing 13. This establishes a passage extending from the injection port 22 to the air communication opening 17 through the micro-flow path 23 for air from the air nozzle unit 100, so that liquid in the micro-flow path 23 can effectively be discharged to the outside of the micro-flow path 23 by injection of air into the injection port 22.

The injection port 22 of the analysis chip 10 is formed at a substantially central position of the substrate 20. This makes it possible to introduce liquid substantially uniformly into the plurality of micro-flow paths 23 connected to the injection port 22.

The micro-flow paths 23 of the analysis chip 10 are formed in a radial pattern to extend from the injection port 22 to the outer edge of the substrate 20. This makes it possible to effectively discharge liquid in the micro-flow paths 23 by means of centrifugal force resulting from rotation of the chip holder 53.

The air communication opening 17 of the analysis chip 10 is arranged inwardly in the radial direction from the opening of the micro-flow path 23 formed at the outer edge of the substrate 20 and where liquid is discharged to the liquid trapping space 16. Specifically, the air communication opening 17 is located inwardly in the radial direction from the exit of the micro-flow path 23 (outer opening part in the radial direction). As a result, liquid having been discharged to the outside of the radial direction from the micro-flow path 23 is prevented from leaking to the outside of the analysis chip 10 through the air communication opening 17.

The biochemical analysis device 50 of this embodiment described above achieves the following effects. The biochemical analysis device 50 includes: the chip holder 53 that allows installation of the analysis chip 10 on the chip holder 53; the chip holder rotation unit 54 that rotates the chip holder 53; the pipetting unit 90 that injects target liquid into the injection port 22 of the analysis chip 10; and the measurement unit 80 that allows measurement of reactions between the target liquid and multiple types of antigens 30 collectively. By making the chip holder rotation unit 54 rotate the chip holder 53, the target liquid having been introduced into the micro-flow path 23 is discharged. Thus, in an analysis device that analyzes target liquid having strong surface tension using the micro-flow paths 23, the target liquid can be discharged rapidly and reliably.

In the biochemical analysis device 50, the chip holder 53 includes the fitting part 531 to make a fit with the analysis chip 10. Thus, the analysis chip 10 can reliably be fixed to the chip holder 53, thereby preventing falling off of the analysis chip 10 from the chip holder 53 to be caused by centrifugal force during rotation.

Further, the analysis chip 10 placed at the chip holder 53 can be rotated properly at a given speed. Additionally, the analysis chip 10 is installed on the chip holder 53 with temperature adjusting means. Thus, in an analysis device such as that of this embodiment requiring incubation under a constant temperature, an increased area of contact between the analysis chip 10 and the chip holder 53 achieves more reliable temperature adjusting control.

In the biochemical analysis device 50, the pipetting unit 90 injects target liquid while the chip holder rotation unit 54 rotates the chip holder 53. Thus, the liquid can be introduced uniformly into the plurality of micro-flow paths 23 connected to the injection port 22. This can prevent the occurrence of a situation where the liquid is introduced unevenly into some of the micro-flow paths 23 or target liquid of a necessary amount cannot be introduced into some of the micro-flow paths 23. As a result, even if the tip portion of the pipetting nozzle 92 (tip of the pipette chip 95) at the liquid injection position deviates from the center of rotation or even if the analysis chip 10 is not placed in a horizontal posture, distances to respective liquid inlets of the micro-flow paths 23 can be substantially equal in response to rotation during the injecting process. This reduces influence on the injecting process by an error of accuracy of the shape of the pipette chip 95 or attachment condition of the pipette chip 95, so that the injecting process can be performed properly.

In the biochemical analysis device 50, the pipetting unit 90 has the pipette chip 95 of a tapered shape. With the pipette chip 95 being inserted into the injection port 22, the pipetting unit 90 injects target liquid. This prevents flying-off of the target liquid over the upper surface of the substrate 20 or its periphery or blockage of the injection port 22 with droplets of the target liquid. As a result, the target liquid can be introduced rapidly into the micro-flow path 23 through the injection port 22.

The biochemical analysis device 50 includes the air nozzle unit 100 that injects air into the injection port 22. This air and rotation of the chip holder 53 work in combination to reliably discharge target liquid in the micro-flow path 23 formed in the analysis chip 10.

The biochemical analysis device 50 makes the air nozzle unit 100 inject air into the analysis chip 10 while rotating the chip holder 53. Thus, even if target liquid is left unremoved in the micro-flow path 23 by the presence of strong surface tension in the micro-flow path 23, such target liquid can reliably be discharged from the micro-flow path 23 with air injected from the air nozzle unit 100.

The present invention is not limited to each aspect of the preferred embodiment of the analysis chip 10 and that of the preferred embodiment of the biochemical analysis device 50 of the present invention described above. Various changes can certainly be devised based on the principles of the present invention.

Figure 15:
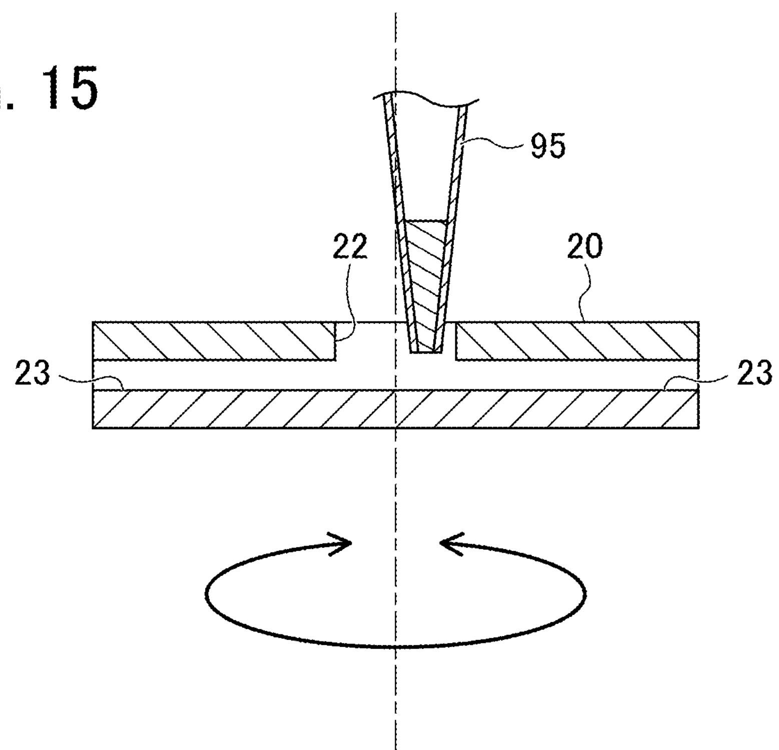
FIG. 15 is a schematic view illustrating a state in outline where a pipetting unit of a biochemical analysis device according to a modification is injecting target liquid into the analysis chip.

According to the configuration of this invention, the liquid injection position is set in such a manner that the tip of the pipette chip 95 substantially agrees with the center of rotation of the chip holder 53. However, the liquid injection position can be set in different appropriate ways. According to a modification described next, the liquid injection position is set in such a manner that the tip of the pipette chip 95 from which target liquid is injected deviates from the center of rotation of the chip holder 53. FIG. 15 is a schematic view illustrating a state in outline where the pipetting unit 90 of a biochemical analysis device according to the modification is injecting target liquid into the analysis chip 10. Illustrations of structures of the analysis chip 10 except the substrate 20 are omitted from FIG. 15. Illustrations of the structures of the biochemical analysis device 50 including the chip holder 53 are also omitted.

As illustrated in FIG. 15, according to the modification, the tip side of the pipette chip 95 from which liquid is pipetted is set at a position deviating from the center of rotation of the chip holder 53. This can be rephrased as follows. As described above, the substrate 20 provided in the analysis chip 10 of this embodiment includes a plurality of micro-flow paths 23 arranged in a radial pattern with respect to the injection port 22. Respective entrances of the micro-flow paths 23 are located at equally-spaced positions from the center of the injection port 22. A liquid injection position of this modification is set at a position deviating from these equally-spaced positions. The pipette chip 95 at the liquid injection position is arranged adjacent to the injection port 22 so as to make liquid pipetted from the tip of the pipette chip 95 contact the inner side surface of the injection port 22. The tip of the pipette chip 95 at the liquid injection position is set so as to be placed below the upper surface of the substrate 20 and so as to form a gap between the tip of the pipette chip 95 and the bottom surface of the injection port 22. Liquid is pipetted toward the chip holder 53 being rotated while the tip of the pipette chip 95 is placed at the liquid injection position. The tip side of the pipette chip 95 at the liquid injection position is approximated in advance to the inner side surface of the injection port 22. Thus, liquid can be injected uniformly and properly into the entrances of the plurality of micro-flow paths 23 formed at the inner side surface of the injection port 22.

Figure 16:
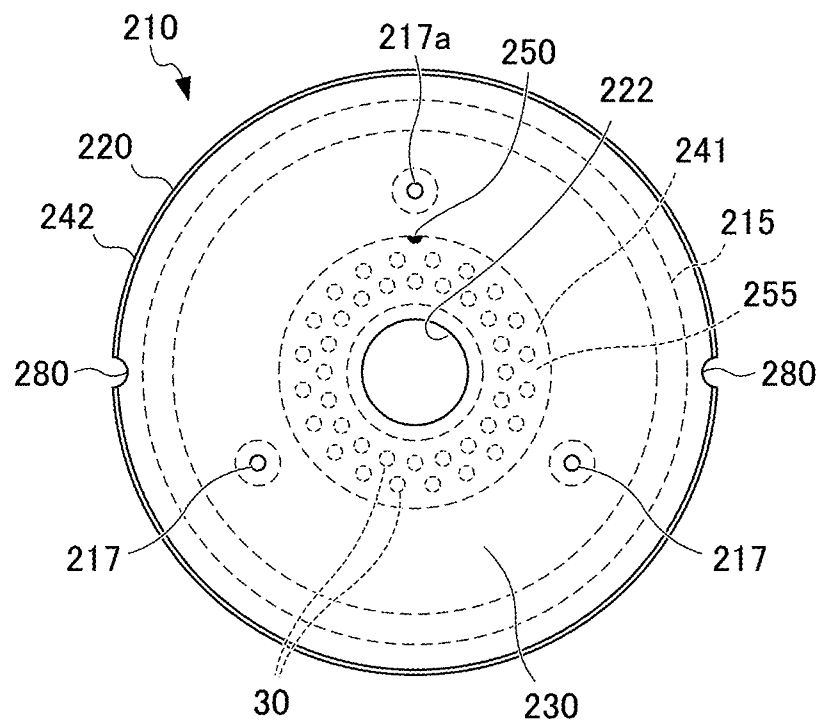
FIG. 16 is a plan view illustrating an analysis chip according to a modification.
Figure 17:
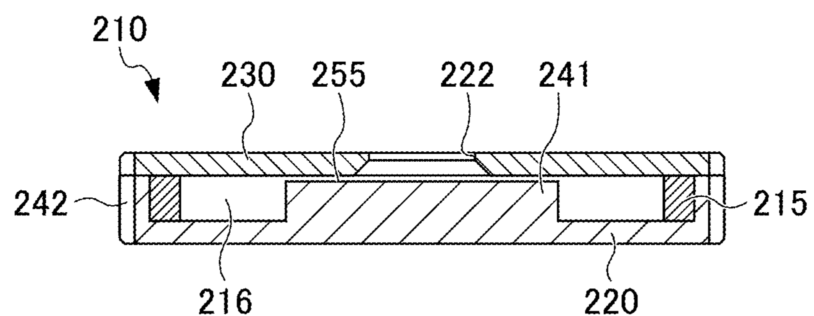
FIG. 17 is a side sectional view schematically illustrating the configuration of the inside of the analysis chip according to the modification.

A modification using an analysis chip 210 having a different configuration from the analysis chip 10 of the aforementioned embodiment is described next. FIG. 16 is a plan view illustrating the analysis chip 210 according to the modification. FIG. 17 is a side sectional view schematically illustrating the configuration of the inside of the analysis chip 210 according to the modification. A biochemical analysis device 50 using the analysis chip 210 has the same configuration as that of the aforementioned embodiment.

The analysis chip 210 of the modification includes a first substrate 220, a second substrate 230, an absorber 215, liquid trapping space 216, an air communication opening 217, and a rotation position reference mark 250.

The first substrate 220 is formed into a disc shape. A circular columnar stage part 241 is formed at the center of the first substrate 220. A wall part 242 is formed to extend over the entire periphery of an end surface of the first substrate 220.

The second substrate 230 is formed into a disc shape using a light-transmitting material. The second substrate 230 is bonded to an upper part of the first substrate 220. A circular injection port 222 for injection of various types of liquid is formed at the center of the second substrate 230. The injection port 222 is formed into a smaller diameter than the stage part 241. Thus, the injection port 222 is accommodated inside the stage part 241 in a plan view. A lower part of the injection port 222 of the second substrate 230 is formed into a tapered shape in a side view that expands further radially at a position closer to the stage part 241 of the first substrate 220.

The upper surface of the stage part 241 of the first substrate 220 and the lower surface of the second substrate 230 form a gap therebetween. The liquid having been injected through the injection port 222 is introduced to the gap by means of capillary action. This gap is formed to extend over the entire outer periphery of the injection port 222. This gap functions as a flow path 255 of the analysis chip 210. In this way, the flow path 255 of the analysis chip 210 is formed into a ring-like shape surrounding the outer periphery of the injection port 222. Thus, the flow path 255 of the analysis chip 210 of this modification can be expressed as a single flow path 255.

In this modification, multiple types of antigens 30 are fixed to the flow path 255 to be close to the stage part 241. The multiple types of antigens 30 are arranged at given intervals in a concentric circular pattern surrounding the injection port 222. The antigens 30 are aligned so as not to overlap each other at least at their centers in a radial direction. By doing so, a distance between the antigens 30 is maintained properly, so that an image of light-emitting reaction can be captured with a high resolution.

Aligning the antigens 30 in the concentric circular pattern is not the only method of fixing the antigens 30. For example, multiple types of antigens 30 may also be arranged irregularly in the flow path 255 of the analysis chip 210 according the modification. Alternatively, a partition may be provided to a part of the flow path 255 to divide the flow path 255 into sector forms. Still alternatively, the antigens 30 may be fixed to the flow path 255 to be close to the second substrate 230. As described above, the method of arranging the antigens 30 can also be changed in this modification.

The absorber 215 is formed of a member having moisture-retaining properties. The absorber 215 is formed into a ring-like shape of a larger diameter than the stage part 241. The liquid trapping space 216 is formed inside the analysis chip 210 to surround the outer peripheral surface of the stage part 241. The absorber 215 is arranged in the liquid trapping space 216 so as to surround the outer peripheral surface of the stage part 241. Target liquid having been discharged from the flow path 255 by means of centrifugal force resulting from rotation of the analysis chip 210 or injection of air by the air nozzle unit 100 is discharged to the liquid trapping space 216 and absorbed by the absorber 215.

The air communication opening 217 includes a plurality of air communication openings 217 formed outside the stage part 241 in a plan view. Air having been injected by the air nozzle unit 100 and having passed through the air communication openings 217 is discharged from the inside of the analysis chip 210 to the outside of the analysis chip 210. An air communication opening 217*a* belonging to the plurality of air communication openings 217 lies on a virtual straight line connecting the center of the analysis chip 210 and the rotation position reference mark 250 to be placed at a position adjacent to the rotation position reference mark 250.

The rotation position reference mark 250 is an indication used for detecting the orientation of the analysis chip 210 and is provided to the first substrate 220. The rotation position reference mark 250 of this modification is provided at one position at the edge of the stage part 241 and has a semicircular shape. The number of the rotation position reference marks 250, and the location and the shape of the rotation position reference mark 250 can be changed, if appropriate. For example, the rotation position reference mark 250 can be provided to the second substrate 230.

The rotation position reference mark 250 is stored in advance in the storage of the control unit 110 as arrangement state determination information corresponding to information about the shape of the analysis chip 210 to be used for identifying a rotation position. Based on the position of the rotation position reference mark 250 in image information acquired by the measurement unit 80 and the arrangement state determination information, the control unit 110 determines the orientation of the rotated analysis chip 210.

In this modification, a positioning notch 280 is formed in each of the first substrate 220 and the second substrate 230. The positioning notch 280 is used for determining the positions of the first substrate 220 and the second substrate 230 when the first substrate 220 and the second substrate 230 are adhesively joined during a step of manufacturing the analysis chip 210. The positioning notches 280 of this modification are formed at positions facing each other across the center of the analysis chip 210. The first substrate 220 and the second substrate 230 are adhesively joined at proper positions determined by the respective positioning notches 280 formed in the first substrate 220 and the second substrate 230. Further, the air communication opening 217*a* formed in the second substrate 230 is adjacent to the rotation position reference mark 250. Thus, whether or not the first substrate 220 and the second substrate 230 are in their proper positions can also be determined by using the air communication opening 217*a*.

The analysis chip 210 of this modification has the aforementioned configuration. The biochemical analysis device 50 analyzes target liquid using the analysis chip 210. Target liquid such as an analyte enters the flow path 255 through the injection port 222 and is introduced into the flow path 255 from an inner side toward an outer side by means of surface tension.

A method of injecting target liquid such as an analyte into the analysis chip 210 and a method of measuring reaction with the antigen 30 are the same as the aforementioned methods. In this modification, the orientation of the rotated analysis chip 210 can be determined accurately based on the rotation position reference mark 250. The type of each reaction is measured based on position information about the multiple types of antigens 30 fixed to the analysis chip 210. The position information about the antigens 30 is information set in advance.

As described above, the analysis chip 210 is formed in such a manner that the flow path 255 surrounds the outer periphery of the injection port 222. By doing so, space around the injection port 222 can be used for arrangement of many types of antigens 30. Further, manufacturing cost can be reduced as a result of a simple configuration of forming the flow path 255 around the injection port 222.

The configuration of the analysis chip 210 according to the modification can be changed, if appropriate. For example, the analysis chip 210 may include a housing to hold the first substrate 220 and the second substrate 230. In this case, the wall part 242 can be omitted from the first substrate 220 and liquid trapping space can be arranged inside the housing and on the outer peripheries of the first substrate and the second substrate. Alternatively, the analysis chip 210 of the modification may include a housing same as the housing of the aforementioned embodiment (including the lower housing 12 and the upper housing 13) and may include an air communication opening in a gap between the housing and the second substrate.

In the biochemical analysis device 50 of this embodiment, the chip holder rotation unit 54 includes the temperature adjustment unit inside the chip holder rotation unit 54. However, the location of a temperature adjustment unit can be changed, if appropriate. For example, a temperature adjustment unit may be provided inside the dark box 81. Additionally, a temperature adjustment unit may be arranged in the dark box 81 in addition to the temperature adjustment unit arranged in the chip holder rotation unit 54. By doing so, the temperature of the analysis chip 10 may be adjusted using a plurality of temperature adjustment units.

The biochemical analysis device 50 of this embodiment can employ an appropriate method of measuring the antigen 30 placed in the micro-flow path 23 of the analysis chip 10 at the measurement position. For example, based on the frequency of rotation of the drive motor for rotating the chip holder 53, reaction may be measured by estimating and determining the arrangement state of the antigen 30 after operation of rotating the analysis chip 10.

In the biochemical analysis device 50 of this embodiment, the amount of suction of target liquid by the pipetting unit 90 is set in a manner that depends on the type of the target liquid. However, this configuration can be changed, if appropriate. For example, the concentration of a reagent solution may be adjusted and the amount of suction (or the amount of injection into the analysis chip 10) may be kept at a constant amount.

The biochemical analysis device 50 of this embodiment is configured to inject air using the air nozzle unit 100 in the liquid discharging process. However, this air injecting process can be omitted in a manner that depends on an analysis target such as an analyte.

The configuration of the analysis chip 10 of this embodiment is such that the antigen 30 as a reactant to react with target liquid is fixed to the substrate 20. Alternatively, an antibody may be fixed. In this way, a reactant to be fixed to the substrate of the analysis chip can be changed, if appropriate, as long as the reactant is a substance to react with target liquid.

The configuration of the analysis chip 10 of this embodiment is not limited to that described in this embodiment but can be changed, if appropriate. For example, the micro-flow paths 23 can be arranged at positions not symmetric with each other.

The configuration of the analysis chip 10 of this embodiment is such that the absorber 15 is arranged in the liquid trapping space 16. However, this configuration can be changed, if appropriate. For example, the analysis chip 10 may also be configured in such a manner that the liquid trapping space 16 is given a structure of trapping liquid and this trapping structure functions to prevent liquid having been discharged from the micro-flow path 23 from returning back into the micro-flow path 23. The analysis chip 10 may also be configured in such a manner that numerous slits are formed in the bottom surface of the liquid trapping space 16 and liquid having been discharged from the micro-flow path 23 is caused to stay in the liquid trapping space 16 by these slits. Alternatively, the absorber 15 may be omitted from the configuration of the analysis chip 10. As described above, a structure for trapping liquid in the liquid trapping space 16 can be changed, if appropriate.

The configuration of the substrate 20 provided in the analysis chip 10 of this embodiment is not limited to the configuration described in this embodiment. The substrate can be formed of a plurality of members. For example, the configuration of the substrate 20 may be such that the micro-flow path 23 is formed by fixing a substrate of a substantially disc shape instead of arranging the film 14 on the lower surface of the substrate 20. As described above, an appropriate configuration can be employed for the substrate 20.

In the description of this embodiment given above, the biochemical analysis device 50 is described as an example of a sample analysis device. However, the present invention is not limited to the biochemical analysis device 50 but is applicable to various types of sample analysis devices. For example, the present invention is also applicable to a sample analysis device to detect trace metal, for example.

EXPLANATION OF REFERENCE NUMERALS

10 Analysis chip
12 Lower housing (housing)
13 Upper housing (housing)
16 Liquid trapping space
17 Air communication opening (communication opening)
18 Opening part
20 Substrate
22 Injection port
23 Micro-flow path (flow path)
30 Antigen (reactant)
50 Biochemical analysis device (sample analysis device)
53 Chip holder
54 Chip holder rotation unit (chip holder rotation mechanism)
80 Measurement unit (measurement device)
90 Pipetting unit (pipetting mechanism)
92 Pipetting nozzle
95 Pipette chip (tip portion)
100 Air nozzle unit (Air injection mechanism)
110 Control unit (controller)
210 Analysis chip
216 Liquid trapping space
220 First substrate (substrate)
222 Injection port
230 Second substrate (substrate)
255 Flow path

The invention claimed is:

1. An analysis chip comprising:

a substrate formed into a substantially disc shape;

an injection port formed at the center of the substrate and through which target liquid as a measurement target is injected; and a flow path that allows introduction of the target liquid into the flow path through the injection port by means of capillary action, wherein multiple types of reactants capable of selectively reacting with a component in the target liquid are fixed to the flow path, the reactants are fixed in the form of spots to the flow path, and the reactants fixed to the flow path each have a shape like a thin film having a substantially flat upper surface.

2. The analysis chip according to claim 1, wherein the flow path of the analysis chip includes a plurality of flow paths arranged in a radial pattern to extend to an outer edge of the substrate, and the multiple types of reactants capable of selectively reacting with a component in the target liquid are fixed to each of the flow paths to be arranged at given intervals.

3. The analysis chip according to claim 1, wherein the analysis chip is formed in such a manner that the flow path surrounds the injection port.

4. The analysis chip according to claim 1, further comprising a housing in which the substrate is arranged and housed, wherein the housing includes:

an opening part where an upper surface of the substrate is exposed at least partially; and liquid trapping space provided inside the housing and on an outer peripheral side of the substrate.

5. The analysis chip according to claim 4, further comprising an absorber arranged in the liquid trapping space and formed of a member having moisture-retaining properties.

6. A sample analysis device comprising:

a chip holder that allows installation of the analysis chip as recited in claim 1 on the chip holder;

a chip holder rotation mechanism that rotates the chip holder;

a pipetting mechanism that injects the target liquid into the injection port of the analysis chip; and a measurement device that allows measurement of reactions between the target liquid and the multiple types of reactants, wherein the target liquid having been introduced into the flow path is discharged by making the chip holder rotation mechanism rotate the chip holder.

7. The sample analysis device according to claim 6, wherein the chip holder includes a fitting part to make a fit with the analysis chip.

8. The analysis chip according to claim 1, wherein the adjacent reactants are formed at positions separated at a distance that is 60% or more of a diameter of the reactant having a smallest diameter among the plurality of reactants fixed.

* * * * *